United States Patent
Mueller et al.

(10) Patent No.: US 9,730,674 B2
(45) Date of Patent: Aug. 15, 2017

(54) SYSTEM AND METHOD FOR LUNG ASSESSMENT

(71) Applicant: General Electric Company, a New York Corporation, Schenectady, NY (US)

(72) Inventors: Frank-Steffen Mueller, Solingen (DE); Alexander Sokulin, Tirat Carmel (IL); Peter Lysyansky, Tirat Carmel (IL)

(73) Assignee: General Electric Company, Schenectady, NY (US)

( * ) Notice: Subject to any disclaimer, the term of this patent is extended or adjusted under 35 U.S.C. 154(b) by 173 days.

(21) Appl. No.: 14/674,050

(22) Filed: Mar. 31, 2015

(65) Prior Publication Data
US 2016/0287217 A1 Oct. 6, 2016

(51) Int. Cl.
*G01N 3/56* (2006.01)
*A61B 8/08* (2006.01)
*A61B 8/00* (2006.01)

(52) U.S. Cl.
CPC .............. *A61B 8/5223* (2013.01); *A61B 8/08* (2013.01); *A61B 8/467* (2013.01)

(58) Field of Classification Search
CPC ................................................. G01N 33/56972
See application file for complete search history.

(56) References Cited

U.S. PATENT DOCUMENTS

2010/0278405 A1* 11/2010 Kakadiaris .......... G06F 19/3431
382/131
2012/0328606 A1* 12/2012 Gossage .......... G01N 33/56972
424/133.1

* cited by examiner

*Primary Examiner* — Joseph M Santos Rodriguez (57) ABSTRACT

An example system includes a probe to generate ultrasound scans; a user interface to receive inputs from and to provide outputs to a user; and a controller to receive selection of an objective value for each of a plurality of lung sectors of a patient and present an objective lung assessment to the user through the user interface.

17 Claims, 8 Drawing Sheets

SYSTEM AND METHOD FOR LUNG ASSESSMENT

BACKGROUND

Rapid lung assessment, such as assessment of lung disorders, is often necessary in environments such as emergency rooms or intensive care units (ICUs) of hospitals, for example. Lung assessment with ultrasound has proven to be a powerful triage resource and a guide for possible treatment of victims. In conventional arrangements, cumbersome and time-consuming imaging and documentation may be required. A user typically documents the observations verbally, which also limits verification or comparison to a standard. For example, such observations may provide a qualitative and, possibly, a subjective assessment that may be subject to vague or incorrect interpretation by another user. In some cases, the condition of a patient's lungs may be assessed multiple times over a period of time to detect an improving or worsening condition. In such cases, a vague interpretation comparison of an earlier assessment may result in wrongly identifying an improving or worsening condition.

BRIEF DESCRIPTION OF THE DISCLOSURE

In one embodiment, a system includes a probe to generate ultrasound scans; a user interface to receive inputs from and to provide outputs to a user; and a controller. The controller is to receive selection of an objective value for each of a plurality of lung sectors of a patient and present an objective lung assessment, such as assessment of a lung condition or disorder, to the user through the user interface.

In one embodiment, a method includes presenting a plurality of assessment options for each of a plurality of lung sectors; receiving a selection of one of the plurality of assessment options for each of the plurality of lung sectors of a patient, the selection being an objective representation of a scan of the lung sector; and presenting an objective lung assessment to the user, the objective lung assessment being a function of the selected assessment options for each of the plurality of lung sectors.

In one embodiment, a computer program product, embodied on a non-transitory computer-readable medium, includes computer code for presenting a plurality of assessment options for each of a plurality of lung sectors; computer code for receiving a selection of one of the plurality of assessment options for each of the plurality of lung sectors of a patient, the selection being an objective representation of a scan of the lung sector; and computer code for presenting an objective lung assessment to the user, the objective lung assessment being a function of the selected assessment options for each of the plurality of lung sectors.

BRIEF DESCRIPTION OF THE DRAWINGS

For a more complete understanding of various examples, reference is now made to the following descriptions taken in connection with the accompanying drawings in which.

DETAILED DESCRIPTION

Various examples described below provide systems and methods for providing lung assessments that are objective and amenable to consistent interpretation. Lung assessments in accordance with the present disclosure allow assessment of lung scans in a manner that avoids vague interpretation.

Figure 1:
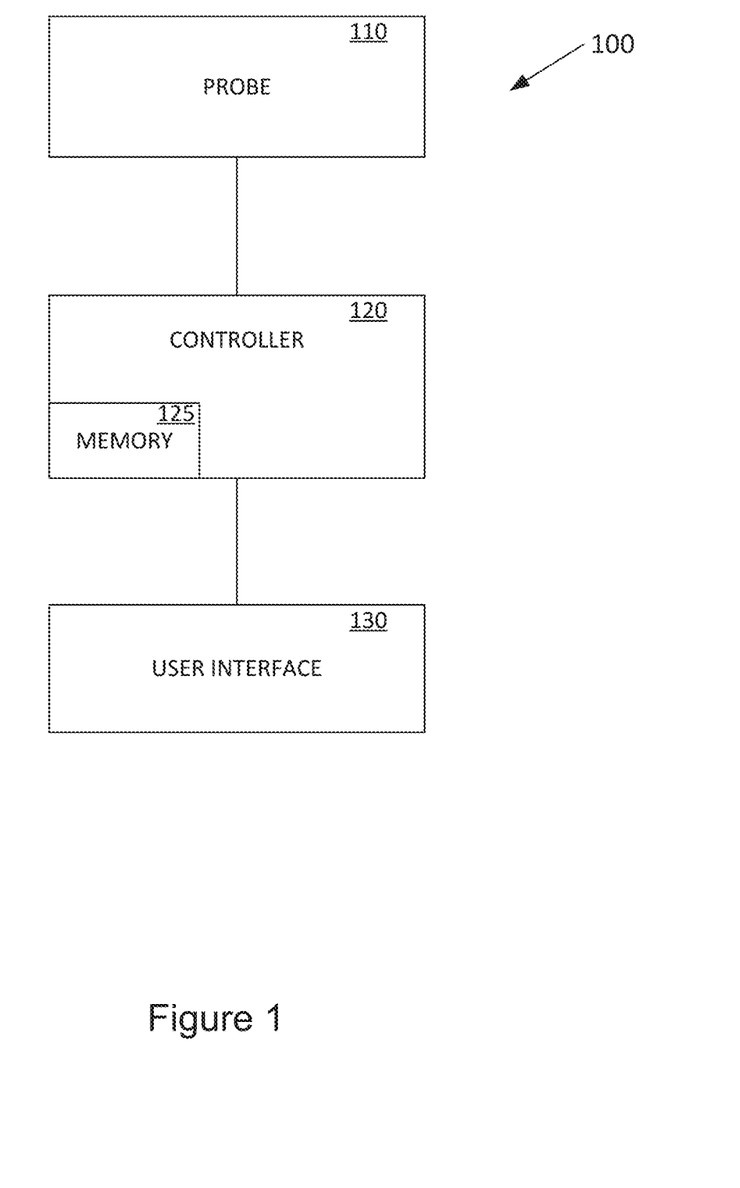
FIG. 1 is a schematic illustration of an example ultrasound system.

Referring now to FIG. 1, an example ultrasound system for lung assessment is schematically illustrated. The illustrated example system 100 includes a probe 110 that may be used to obtain ultrasound images from, for example, a patient. In various examples, the probe may be a handheld device that may be operated by a user, such as a physician or an emergency medical technician. Such probes are well known to those skilled in the art, and a detailed description of such probes is unnecessary for an understanding of the scope of the present disclosure.

The example system 100 of FIG. 1 includes a central controller 120 to control various operations of the system 100. In various examples, the controller 120 may be a central processing unit and may further include other components, such as a storage unit. In the example illustrated in FIG. 1, the storage unit is a memory 125 for storing various types of information including, but not limited to, data and instructions (e.g., program code) executable by the controller 120. In other examples, the storage unit may be an external database (not shown in FIG. 1) which may be shared by the central controller 120 of the example system 100, as well as one or more other such systems. In various examples, the technical effect of the controller 120 is to execute a lung protocol which allows users, such as emergency room personnel, to efficiently assess the condition of a patient and provide assessments which may be interpreted in an objective or standardized manner.

The example ultrasound system 100 of FIG. 1 includes a user interface 130 to allow interaction of the example system 100 with a human user. In various examples, the user interface 130 may include various forms, such as a touchscreen interface which outputs information to the user in the form of a display and receives input from the user through touches or clicks on a screen. In other examples, the user interface 130 may include a display for output and a keyboard and/or a mouse for receiving inputs from the user. Those skilled in the art will appreciate that various other forms of user interfaces are possible and are contemplated within the scope of the present disclosure.

Figure 2:
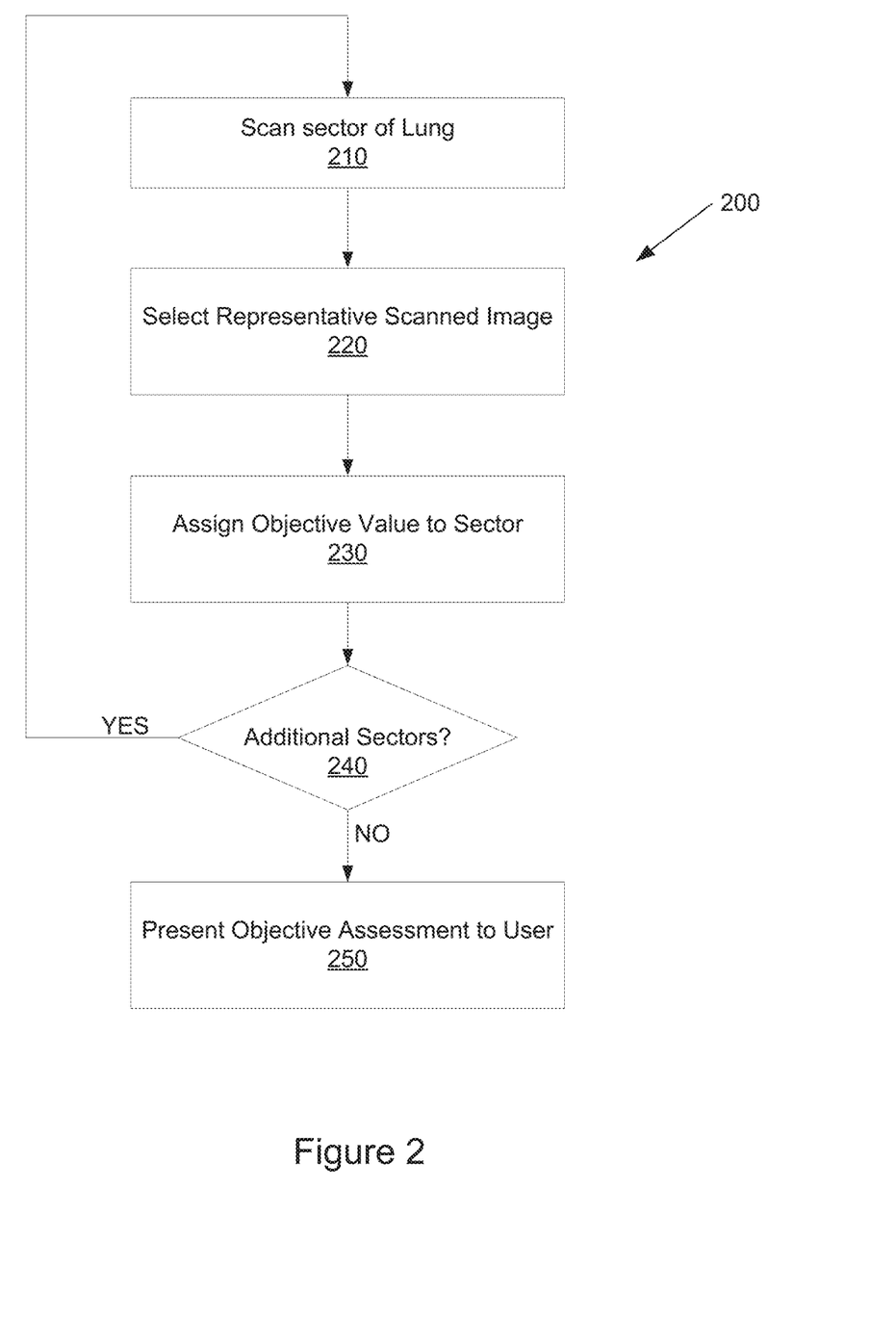
FIG. 2 is a flowchart illustrating an example method for lung assessment.

Referring now to FIG. 2, a flowchart illustrates an example method 200 for lung assessment using, for example, the example ultrasound system 100 illustrated in FIG. 1. The example method of FIG. 2 may be implemented in a variety of environments, including emergency rooms, ICUs or in the field by an emergency medical technician, for example. Further, the example method 200 of FIG. 2 may be implemented using a variety of systems including that illustrated in FIG. 1, as well as a variety of other devices and systems. The example method 200 of FIG. 2 may begin with a user scanning a sector of a lung of a patient (block 210). The scanning of a sector of the lung may be achieved using the probe 110 of FIG. 1, for example. In various examples, the probe 110 may be positioned on a selected sector of a lung. In this regard, scanning of a lung may be divided into a variety of sectors, some examples of which are described below with reference to FIGS. 3 and 4.

Figure 3:
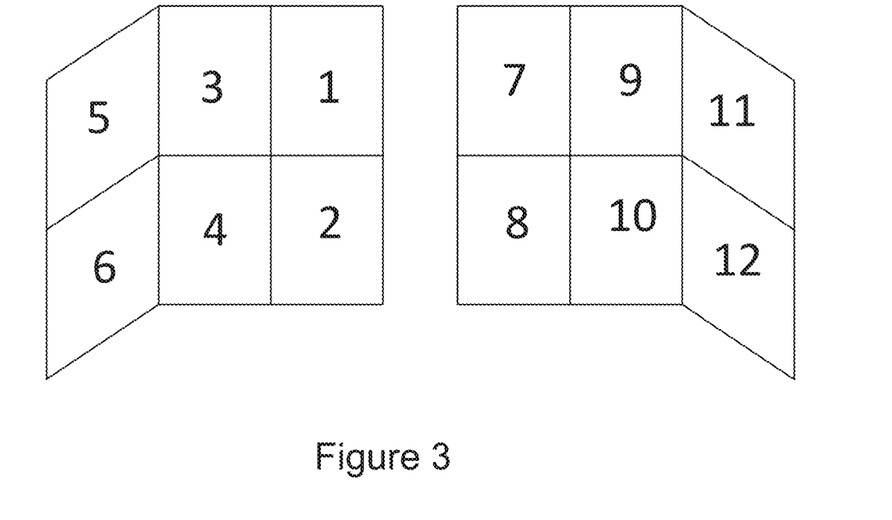
FIGS. 3 and 4 illustrate example sector maps for lung assessment.
Figure 4:
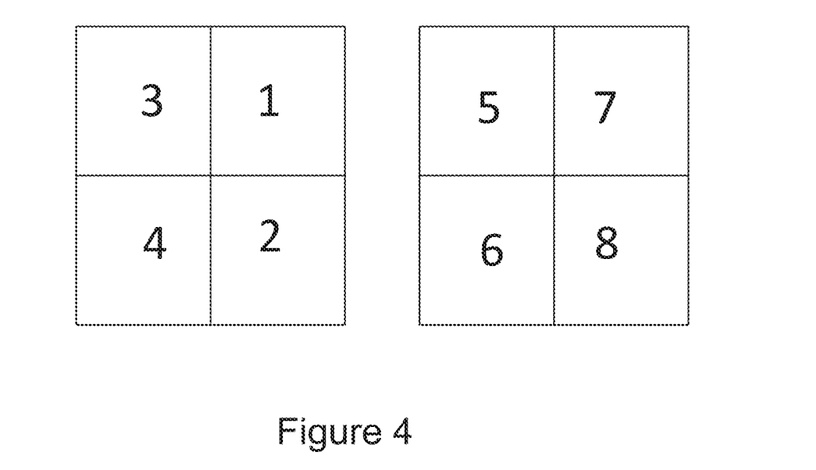

In one example, as illustrated in FIG. 3, each lung may be divided into six sectors, for a total of 12 sectors. Sectors one through six may correspond to the left lung, while sectors seven through 12 may correspond to the right lung, or vice versa, for example. In another example, as illustrated in FIG. 4, each lung may be divided into four sectors. Sectors one through four may correspond to the left lung, while sectors five through eight may correspond to the right lung, or vice versa, for example. Of course, in other examples, any of a variety of other arrangements of sectors may be used. The scope of the present disclosure is not limited to any particular arrangement or division of sectors.

Referring again to FIG. 2, during scanning of a sector of the lung (block 210), one or more scan images may be stored, for example, in the memory 125 of the system 100 of FIG. 1. In various examples, the number of images stored for each sector may vary and may be selected by the user or determined by the controller 120 of the system 100. For example, the controller 120 may store images at a regular interval of time during the scan.

Figure 5:
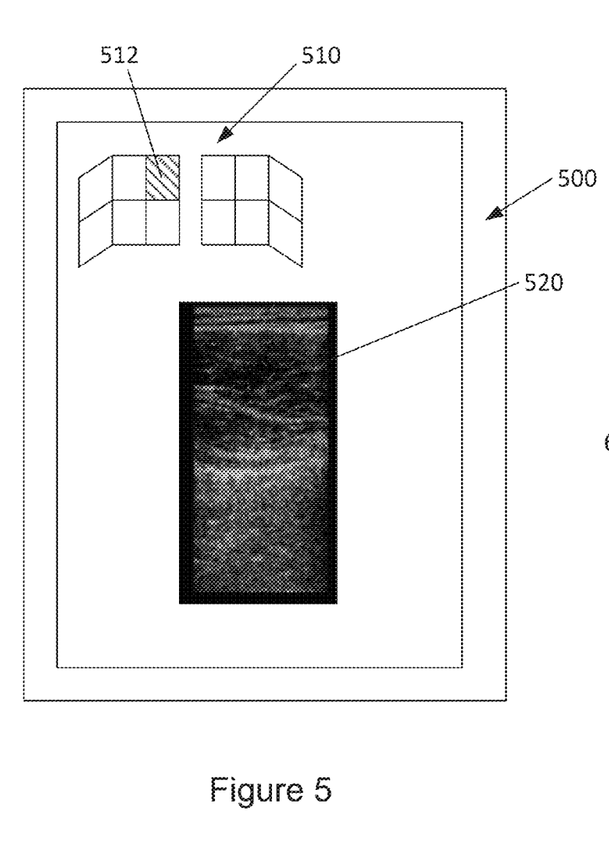
FIG. 5 is an example display illustrating scanning of a lung.

At block 220, the user may select a representative scanned image from the images stored during the scanning of block 210. Reference is made to FIG. 5 which illustrates an example display 500 which may be presented to the user. The example display 500 of FIG. 5 includes a sector layout region 510 which may highlight the sector of the lung being currently scanned, such as the sector 512. The example display 500 of FIG. 5 may further include an image region 520. In selecting a representative image, as in block 220 of FIG. 2, the user may scroll through a series of images which were stored during the scan at block 210, for example. As noted above, in various examples, a user interface may be provided with a touchscreen to allow the user to interact with the system 100 of FIG. 1. In this regard, the user may scroll through the images in the image region 520 by, for example, swiping the display 500, and may select an image by clicking or tapping the desired image.

In various examples, the image region 520 presents a still image from the scanning of the sector. In other examples, a video clip may be looped in the image region 520.

The representative image selected by the user may be representative of the state of the sector of the lung being observed by the user, for example. In this regard, the user may use his best judgment in selecting the representative image. Additionally, the user may take into account the quality of the scanned image, such as focus, fuzziness, etc.

Referring again to FIG. 2, the user may assign an objective value to the scanned image selected at block 220 (block 230). In various examples, the objective value may be based on a standardized scoring system, examples of which are described in detail below with reference to FIGS. 6 and 11. Example scoring systems may include numerical values (e.g., 0, 1, 2 or 3, as described in FIG. 6 below) or standardized conditions (normal aeration, interstitial syndrome, pleural effusion, consolidation, pneumothorax, etc.) for the objective values. As noted above, assigning an objective value to an observed image provides for consistency in the assessment of the condition of the lung, or the sector scanned. In accordance with the present disclosure, objective values may take several forms. Two such forms are described below with reference to FIGS. 6 and 11, each of which is discussed in greater detail below. However, those skilled in the art will appreciate that various other forms of objective values are possible and are contemplated within the scope of the present disclosure.

Referring again to FIG. 2, a determination may be made as to whether or not additional sectors remain to be scanned (block 240). If additional sectors remain to be scanned, the user may select the next sector to be scanned by, for example, tapping a next sector in the sector layout region 510. The method 200 may then return to block 210 for scanning of the next sector of the lung. If, on the other hand, the determination is made at block 230 that all sectors have been scanned and no sectors remain, the method may proceed to block 250 of FIG. 2.

In the example described in FIG. 2, objective values are assigned to each sector (block 230) immediately following the scanning and or selection of a scanned image for that sector before proceeding to any remaining sectors. In other examples, all sectors may be scanned before assigning of an objective value to each sector.

Following the assigning of an objective value to each sector, an objective assessment for the entire lung may be presented to the user (block 250). In this regard, an assessment of the lung based on the assignment of objective values to each sector may be generated. The objective assessment may be presented to the user as a graphic, a score or other such presentation to the user and/or may be stored for retrieval by other users. For example, the observation and assigning of the scores to the various sectors (e.g., blocks 210-240 of FIG. 2) may be performed by a technician, and the objective assessment based on such observation and assigning of scores may be retrieved and viewed by a physician. Various examples of objective assessments of the entire lung are described below with reference to FIGS. 7, 8 and 12.

In various examples, the user may be presented with a summary of the health of the lungs in various forms. In this regard, the user may be provided with the ability to see the observed state of the lungs in such a manner that another user may be able to receive the state of the lungs in a standardized and/or quantitative manner. Two such examples in accordance with the present disclosure are described below.

Figure 6:
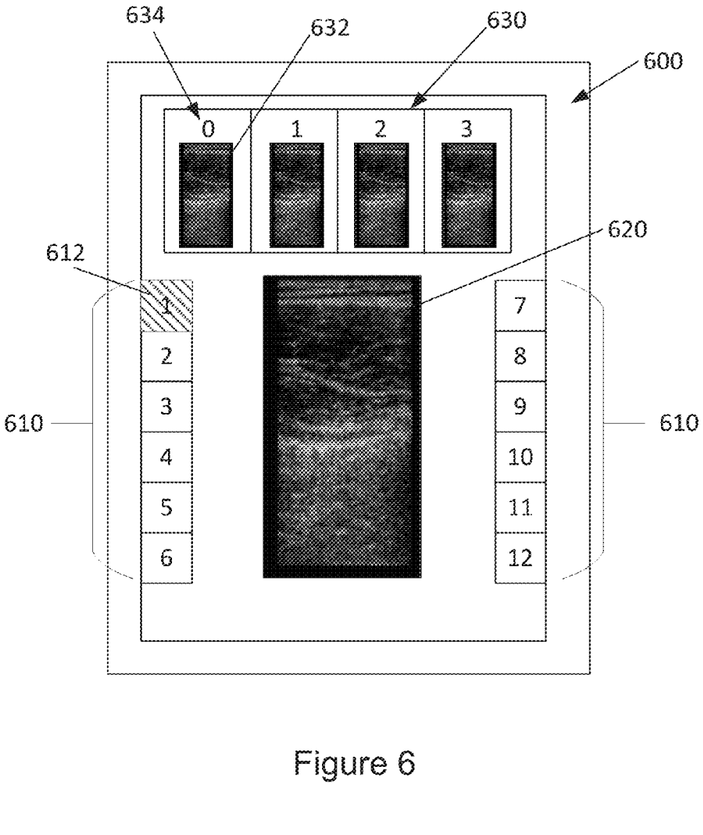
FIG. 6 is an example display illustrating assigning of a score to a sector of a lung.
Figure 7:
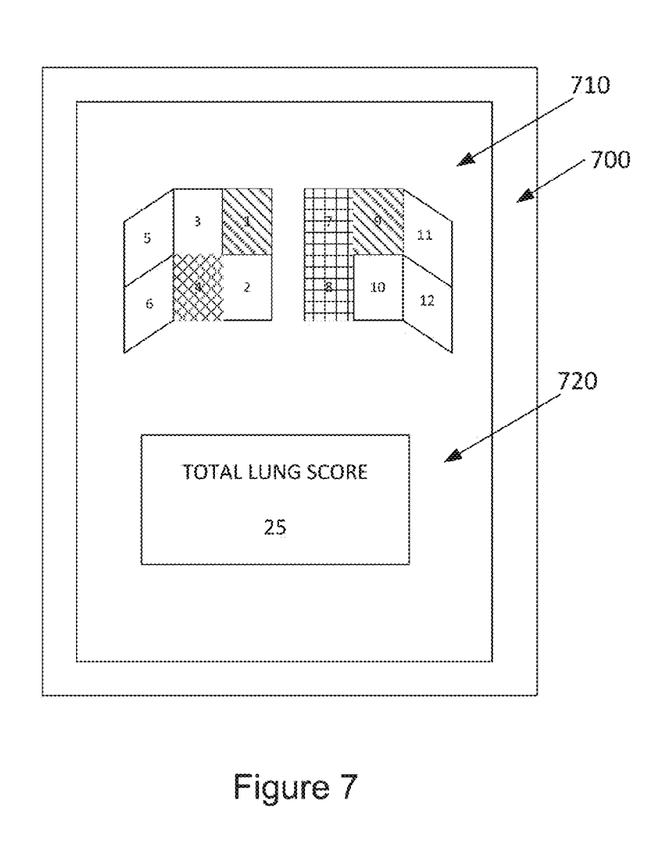
FIG. 7 is an example display illustrating providing a lung assessment to a user.
Figure 8:
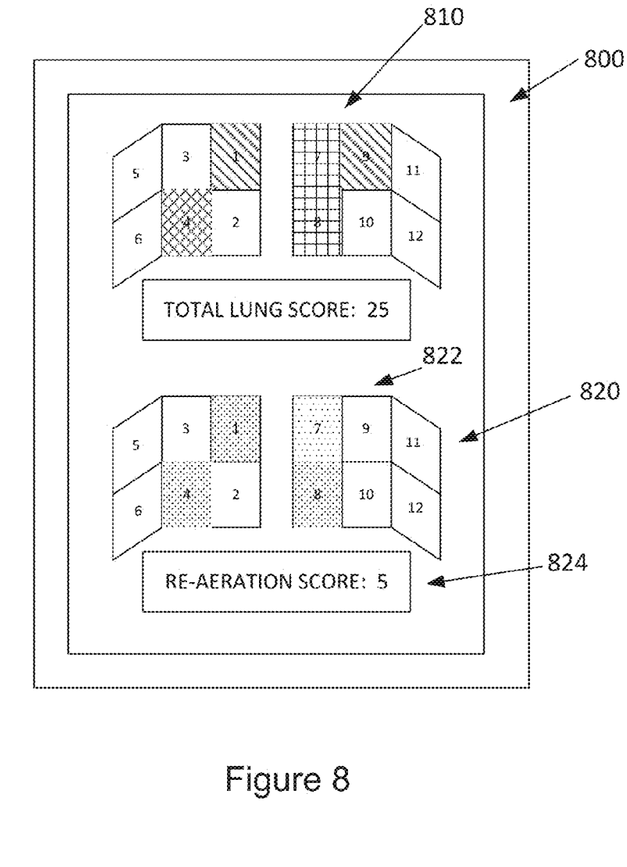
FIG. 8 is another example display illustrating providing a lung assessment to a user.

Referring first to FIGS. 6-8, one example implementation of the process of FIG. 2 is described. As noted above with reference to block 230 of FIG. 2, an objective value may be assigned to a scanned image of each sector of the lung. FIG. 6 illustrates an example score selection display 600 that may be used for assigning of an objective value or score to various sectors of a lung. The example display of FIG. 6 includes a sector selection region 610. The sector selection region 610 includes icons representative of each sector of the lung, sectors 1-12 in the illustrated example. A user may select a sector for assigning of an objective score by, for example, clicking on or touching the icon corresponding to the desired sector. In the example of FIG. 6, sector one 612 is shown as having been selected.

Upon selection of a sector in the sector selecting region 610, a scanned image of the patient's lung is displayed in an image region 620. For example, the image displayed in the image region 620 may be the image selected as the representative scanned image in block 220 of FIG. 2.

In addition to the sector selecting region 610 and the image region 620, the example score selection display 600 of FIG. 6 also includes a score card portion 630. The score card portion 630 of the example score selection display 600 includes a variety of score guides 630 for selection by the user. The score guides 630 provide the user with an objective or standardized basis for assigning a value to the scanned image 620 being scored. In the example of FIG. 6, each score guide 630 includes an objective image 632 and an objective score 634. The objective images 632 may be library images which correspond to various conditions of the lung. In one example, each library image represents a typical image corresponding to the health of a sector of the lung. In various examples, the library images may be a set of standardized images that may be familiar to various users. In some examples, the objective images 632 may be still images, while in other examples, the objective images 632 may include a loop of a video clip.

In the example of FIG. 6, a set of four score guides 630 are displayed to the user, each score guide 630 representing a different condition of the lung. Each score guide 630 includes an objective image 632 and an objective score 634. A score guide 630 with an objective score 634 of "0" corresponds to a lung sector in good health and, accordingly, may be accompanied with an objective image 632 showing a typical scan of a lung sector in good health. Similarly, objective scores 634 of 1, 2 or 3 may be accompanied with objective images 632 showing typical scans of lung sectors in progressively worse health.

In one example, the objective images 632 may be retrieved from a library of images. The library may be stored, for example, in the memory 125 of the example system 100 of FIG. 1. In one example, the same objective images 632 may be displayed for each lung sector. In other examples, the objective images 632 displayed to the user may depend on the sector selected by the user from the sector selection region 610. In this regard, the objective images 632 may be typical scans of the corresponding sectors of the lung.

Those skilled in the art will appreciate that, while the example of FIG. 6 includes assigning objective scores as numerical values, other types of objective scores are possible and are contemplated within the scope of the present disclosure.

In one example, the protocol may be automated to facilitate simpler and faster assessment. In this regard, upon scanning of a sector, the system may automatically identify the sector being scanned. Upon completion of scanning of the sector, the example screen of FIG. 6 may be displayed to the user with the active sector (e.g., sector 1 612) already selected. Further automation may be provided by selection or suggestion of an objective image 632 and an objective score 634 from the score guide 630. Of course, those skilled in the art will appreciate that various other steps in the assessment process may be automated. For example, the system may automatically label each scanned image with appropriate identifiers, such as the identity of the patient, time and location of the scan, the name of the technician performing the scan, the region or sector being scanned, etc. Such automated labeling may be beneficial when scanned images may look similar to one another, as in the case of various thoracic areas.

The user may select the objective image 632 which most closely corresponds to the scanned image 610, thus assigning an objective score to the selected sector. In various examples, once a user has assigned an objective score to each sector of the patient's lungs, the user may be provided with an objective assessment of the lungs. FIG. 7 illustrates an example assessment display 700 for providing a lung assessment to a user. The example assessment display 700 includes a graphic assessment 710 and a numerical assessment 720. Various examples may provide only the graphic assessment 710, only the numerical assessment 720 or both, as illustrated in the example of FIG. 7.

The example graphical assessment 710 of the objective assessment display 700 may include a sector layout with each sector appropriately highlighted. The highlighting of each sector in the sector layout may correspond to the assigned objective score 634 for that sector, as shown in FIG. 6. In one example, the highlighting may include shading of the sector in the sector map. Heavier shading may correspond to a higher assigned objective score 634 (worse health). For example, a sector with an assigned objective score of 0 may have no shading, while a sector with an assigned objective score of 4 may have very heavy shading. In other examples, the highlighting may be color coded. For example, a sector with an assigned objective score of 0 may be colored green, a sector with an assigned objective score of 1 may be colored yellow, a sector with an assigned objective score of 2 may be colored orange, and a sector with an assigned objective score of 3 may be colored red.

The example numerical assessment 720 of the objective assessment display 700 may be a numerical value that is a function of the assigned objective scores of the various sectors. In one example, the numerical assessment 720 may be an arithmetic sum of the objective scores of the twelve sectors. In other examples, other functions may be used to provide an objective numerical assessment 720 or a standardized qualitative assessment representative of the condition of the lungs to be displayed to the user.

In one example, in addition to the current health of the lungs, a change in the health of the lungs from a previous scan and/or objective score may be provided to the user. For example, FIG. 8 illustrates an example assessment display 800 illustrating providing a lung assessment 810 to a user in a manner similar to that described above with reference to FIG. 7. In addition, the example assessment display 800 of FIG. 8 includes a re-aeration assessment 820 to provide the user with a temporal dimension. In the example of FIG. 8, the re-aeration assessment 820 may include a graphic re-aeration assessment 822 and a numerical re-aeration assessment 824. The graphic re-aeration assessment 822 may include shading and/or coloring of the various sectors to illustrate a change in the assigned objective score of the individual sectors. Similarly, the numerical re-aeration assessment 824 may be a numerical value that is a function of the change in the numerical assessment (e.g., numerical assessment 720 of FIG. 7). In one example, the numerical re-aeration assessment 824 may be a simple difference in the numerical assessments. In other examples, a different mathematical function may be used to calculate the numerical re-aeration assessment 824.

Figure 9:
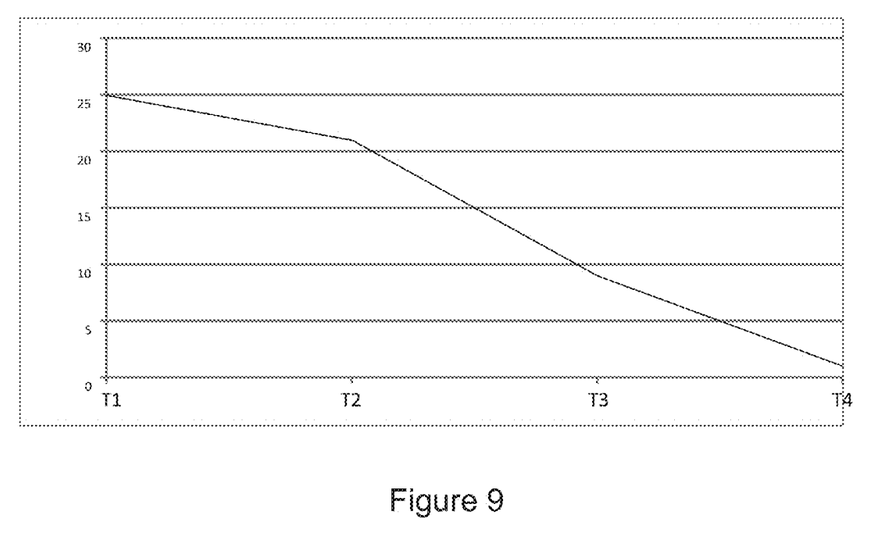
FIGS. 9 and 10 are example displays illustrating lung assessment over a period of time.
Figure 10:
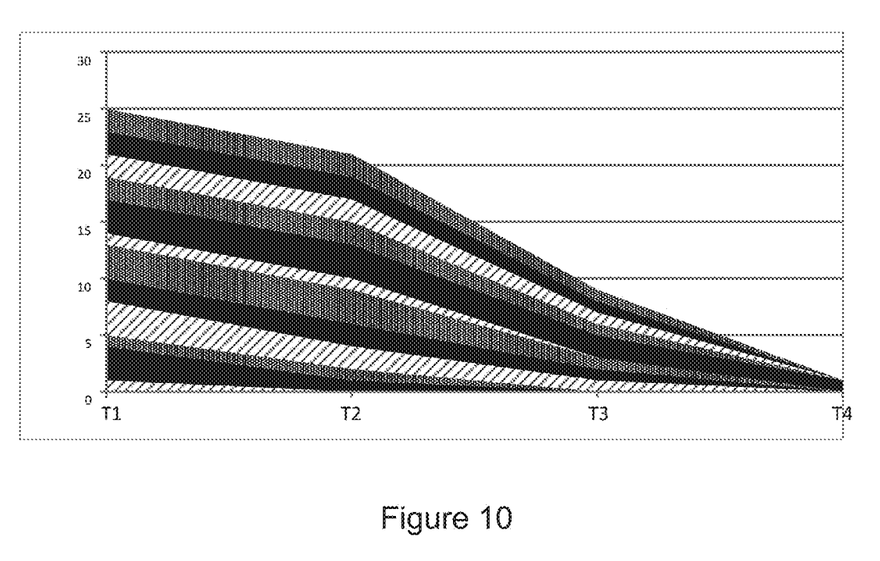

The temporal dimension may be conveyed to the user in a variety of manners. FIGS. 9 and 10 illustrate two examples of displays for presenting to a user an objective assessment of a patient's lungs over multiple scans and/or assessments. In various examples, a patient's lungs may be scanned and an initial objective assessment may be provided and/or stored. One or more treatments may be prescribed to the patient, and the effectiveness of the treatments may be monitored via additional scans and objective assessments. As illustrated in FIG. 9, an example display may provide the user with a graph of the objective assessment of the patient at various times and/or various scans. In another example, as illustrated in FIG. 10, the graph may indicate the assigned scores of each sector of the lung. In the case where the objective assessment is a sum of the assigned scores of the various sectors, the example graph of FIG. 10 also provides the user with the objective assessment at various times and/or various scans.

Figure 11:
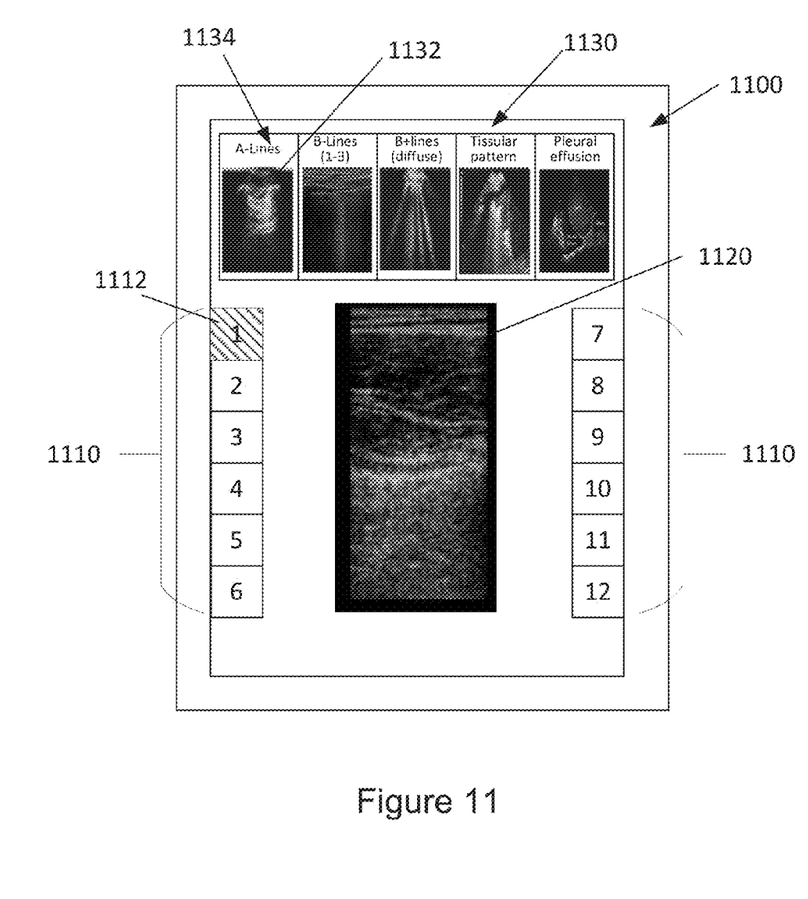
FIG. 11 is an example display illustrating assessment of a lung.
Figure 12:
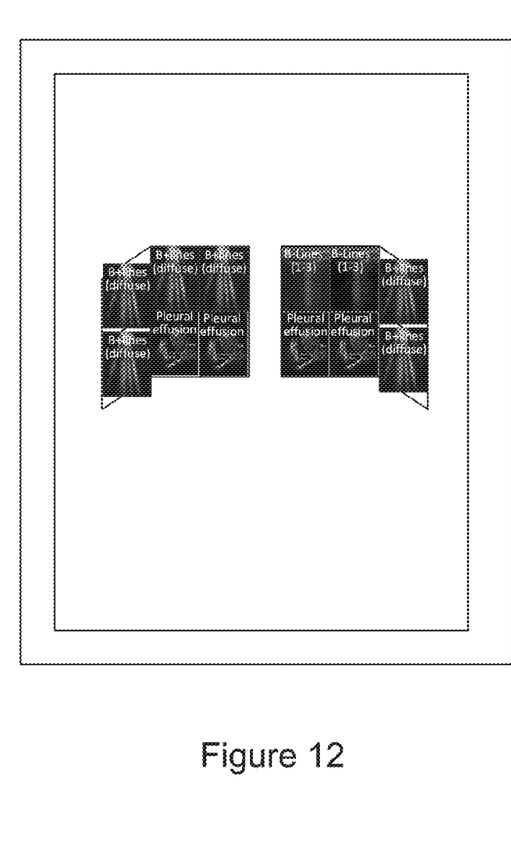
FIG. 12 is an example display illustrating providing a lung assessment to a user.

Referring now to FIGS. 11 and 12, another example implementation of the process of FIG. 2 is described. As noted above with reference to block 230 of FIG. 2, an objective value may be assigned to a scanned image of each sector of the lung. FIG. 11 illustrates an example sector assessment display 1100 that may be used for assigning of an objective value to various sectors of a lung. The example sector assessment display 1100 of FIG. 11 includes a sector selection region 1110. The sector selection region 1110 is similar to the sector selection region 610 described above with reference to FIG. 6 and includes icons representative of each sector of the lung, sectors 1-12 in the illustrated example. A user may select a sector for assigning of an objective value by, for example, clicking on or touching the icon corresponding to the desired sector. In the example of FIG. 11, sector one 1112 is shown as having been selected.

Upon selection of a sector in the sector selecting region 1110, a scanned image of the patient's lung is displayed in an image region 1120. As in the example of FIG. 6, the image displayed in the image region 1120 may be the image selected as the representative scanned image in block 220 of FIG. 2.

The example sector assessment display 1100 of FIG. 11 also includes an assessment selection portion. The example assessment selection portion of FIG. 11 includes a variety of assessment options 1130 for selection by the user. The assessment options 1130 provide the user with an objective or standardized basis for assigning a value, or assessment, to the scanned image 1120 being assessed. In the example of FIG. 11, each assessment option 1130 includes an objective image 1132 and a corresponding objective assessment 1134. As with the example of FIG. 6 described above, the objective images 1132 may be library images which correspond to various conditions of the lung. In some examples, the objective images 1132 may be still images, while in other examples, the objective images 1132 may include a loop of a video clip.

In the example of FIG. 11, a set of five assessment options 1130 are displayed to the user, each assessment option 1130 representing a different condition of the lung. Each assessment option 1130 includes an objective image 1132 and an objective assessment 1134. While the example of FIG. 6 uses numerical scores, the example of FIG. 11 provides objective assessments 1134 which include a clinical description of the condition of each sector. For example, the objective assessments 1134 accompanying the objective images 1132 may include "A-lines," "B-lines (1-3)," "B+lines (diffuse)", "Tissular pattern" and "Pleural effusion." Of course, other examples may include more or different objective assessments compared to those illustrated in FIG. 11.

The user may select the objective assessment 1132 which most closely corresponds to the scanned image 1120, thus assigning an objective value to the selected sector. In various examples, once a user has assigned an objective value to each sector of the patient's lungs, the user may be provided with an objective assessment of the lungs. FIG. 12 illustrates an example assessment display for providing a lung assessment to a user. The example assessment display of FIG. 12 includes a graphic assessment of the lungs. The graphic assessment may include a sector layout of the lungs, with each sector including the assigned objective assessment. In the example of FIG. 12, the assigned objective assessment is superimposed on the scanned image (e.g., scanned image 1120 of FIG. 11) for each sector. Thus, the user is provided with the actual scanned image of the sector, along with an objective assessment of each sector.

Figure 13:
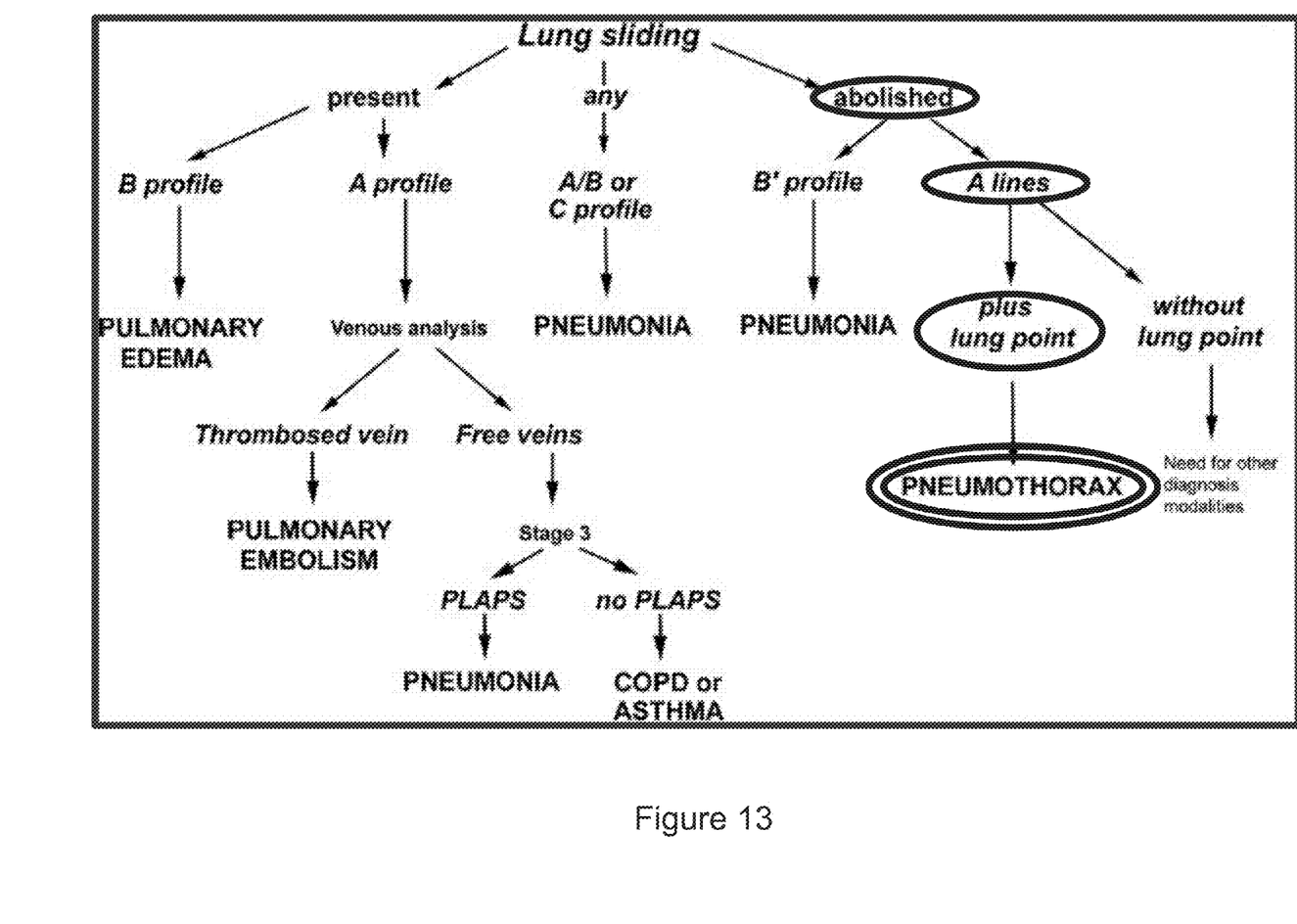
FIG. 13 is an example display illustrating providing an example diagnosis tree to a user.

In one example, based on the objective assessment of the sectors, as illustrated in FIGS. 11 and 12, a diagnosis tree may be provided to the user, highlighting the path leading to the diagnosis. One such example diagnosis tree is illustrated in FIG. 13. Selection of objective assessments 1132, as illustrated in FIG. 11, may result in conditions on the diagnosis tree being highlighted, as shown circled in FIG. 13. The resulting path leads to the ultimate diagnosis, shown with double circles in FIG. 13.

In some examples, the monitoring of the lung may be combined with other parameters for a more complete assessment. For example, the aeration or re-aeration of the lung may be combined with such parameters as the patient's vital signs. Other parameters may include quantity of fluid intake and output, patient's weight, weight gain or loss, for example. Of course, those skilled in the art will appreciate that various other parameters are possible and are contemplated within the scope of the present disclosure.

The various examples set forth herein are described in terms of example block diagrams, flow charts and other illustrations. Those skilled in the art will appreciate that the illustrated examples and their various alternatives can be implemented without confinement to the illustrated examples. For example, block diagrams and their accompanying description should not be construed as mandating a particular architecture or configuration.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An ultrasound system, comprising:
a memory;
a probe to generate ultrasound scans and store the ultrasound scans in the memory;
a user interface to receive inputs from and to provide outputs to a user, the user interface including a display for outputting information; and
a controller configured to:
 display, on the display, a sector selection region including a plurality of icons, where each of the plurality of icons represents one of a plurality of lung sectors; a plurality of score guides, where each of the plurality of score guides includes an objective image and an objective score; an image region for displaying images representing the plurality of lung sectors;
 receive selection of an objective value for each one of the plurality of lung sectors through the user input, where the selection of the objective value for each one of the plurality of lung sectors comprises:
  receiving an input through the user interface to select a desired one of the plurality of lung sectors;

highlighting one of the plurality of icons representing the desired one of the plurality of lung sectors on the display in response to receiving the input; and displaying an image representing the desired one of the plurality of sectors of the lung in the image region in response to receiving the input; and present an objective lung assessment to the user through the display, the objective lung assessment comprising a sector layout representing the plurality of lung sectors, where a color coding or a shading is used to identify the objective value selected for each of the plurality of lung sectors in the sector layout.

2. The system of claim 1, wherein the selection of the objective value for each one of the plurality of lung sectors is one of a plurality of options presented to the user in the plurality of score guides.

3. The system of claim 2, wherein the plurality of options presented to the user include a plurality of objective images, each objective image corresponding to an objective value.

4. The system of claim 1, wherein the objective value for each one of the plurality of lung sectors includes a numerical score.

5. The system of claim 4, wherein the objective lung assessment includes a total numerical score based on the numerical scores of each of the plurality of lung sectors.

6. The system of claim 4, wherein the objective lung assessment includes a comparison to a previous objective lung assessment.

7. The system of claim 1, wherein the objective value for each of the plurality of lung sectors includes a clinical description.

8. The system of claim 7, wherein the objective lung assessment includes a diagnosis tree highlighting a diagnosis based on the clinical description of one or more sectors.

9. A method for lung assessment with an ultrasound system, comprising:
generating ultrasound scans with a probe;
storing the ultrasound scans in a memory;
displaying, on a display, a sector selection region including a plurality of icons, where each of the icons represents one of a plurality of lung sectors; a plurality of score guides, where each of the plurality of score guides includes an objective image and an objective score; and an image region for displaying images representing the plurality of lung sectors;
selecting an objective value for each one of the plurality of lung sectors, where the selection of the objective value for each one of the plurality of lung sectors comprises:
receiving an input through a user interface to select a desired one of the plurality of lung sectors;
highlighting one of the plurality of icons representing the desired one of the plurality of lung sectors on the display in response to receiving the input; and
displaying an image representing the desired one of the plurality of lung sectors in the image region in response to receiving the input; and
presenting an objective lung assessment to the user through the display, where the objective lung assessment comprises a sector layout representing the plurality of lung sectors, where a color coding or a shading is used to identify the objective value selected for each of the plurality of lung sectors represented in the sector layout.

10. The method of claim 9, wherein the selection of the objective value for each of the plurality of lung sectors is one of a plurality of options presented to the user.

11. The method of claim 10, wherein the plurality of options presented to the user include a plurality of objective images, each objective image corresponding to an objective value.

12. The method of claim 9, wherein the objective value for each of the plurality of lung sectors includes a numerical score.

13. The method of claim 12, wherein the objective lung assessment includes a total numerical score based on the numerical scores of each of the plurality of lung sectors.

14. The method of claim 13, wherein the objective lung assessment includes a comparison to a previous objective lung assessment.

15. The method of claim 9, wherein the objective value for each of the plurality of lung sectors includes a clinical description.

16. The method of claim 15, wherein the objective lung assessment includes a diagnosis tree highlighting a diagnosis based on the clinical description of one or more sectors.

17. A computer program product, embodied on a non-transitory computer-readable medium, comprising:
computer code for controlling a probe to generate ultrasound scans;
computer code for storing the ultrasound scans in a memory;
computer code for displaying on a display, a sector selection region including a plurality of icons, where each of the icons represents one of lung sectors; a plurality of score guides, where each of the plurality of score guides includes an objective image and an objective score; and an image region for displaying images representing the plurality of lung sectors;
computer code for receiving a selection of an objective value for each one of the plurality of lung sectors, wherein receiving the selection of the objective value for each one of the plurality of lung sectors comprises:
receiving an input through a user interface to select a desired one of the plurality of lung sectors;
highlighting one of the plurality of icons representing the desired one of the plurality of lung sectors on the display in response to receiving the input; and
displaying an image representing the desired one of the plurality of lung sectors in the image region in response to receiving the input; and
computer code to present an objective lung assessment to the user through the display, where the objective lung assessment comprises a sector layout representing the plurality of sectors of the lung, where each of the sectors is colored or shaded based on the objective values received for each of the plurality of sectors.

* * * * *